United States Patent
Rathmacher et al.

(10) Patent No.: US 10,772,856 B2
(45) Date of Patent: Sep. 15, 2020

(54) COMPOSITIONS AND METHODS OF USE OF BETA-HYDROXY-BETA-METHYLBUTYRATE (HMB) FOR DECREASING FAT MASS

(71) Applicant: Metabolic Technologies, Inc., Ames, IA (US)

(72) Inventors: John Rathmacher, Story City, IA (US); Naji Abumrad, Nashville, TN (US); Shawn Baier, Polk City, IA (US)

(73) Assignee: Metabolic Technologies, Inc., Ames, IA (US)

( * ) Notice: Subject to any disclaimer, the term of this patent is extended or adjusted under 35 U.S.C. 154(b) by 0 days.

(21) Appl. No.: 15/840,638

(22) Filed: Dec. 13, 2017

(65) Prior Publication Data
US 2018/0098951 A1  Apr. 12, 2018

Related U.S. Application Data

(62) Division of application No. 15/170,329, filed on Jun. 1, 2016, now abandoned.

(60) Provisional application No. 62/169,334, filed on Jun. 1, 2015.

(51) Int. Cl.
*A61K 31/19* (2006.01)

(52) U.S. Cl.
CPC ................................ *A61K 31/19* (2013.01)

(58) Field of Classification Search
CPC ....... A61K 31/19; A61K 31/215; A61K 31/22
See application file for complete search history.

(56) References Cited

U.S. PATENT DOCUMENTS

| | | |
|---|---|---|
| 5,028,440 A | 7/1991 | Nissen |
| 6,031,000 A * | 2/2000 | Nissen ................. A61K 31/195 514/557 |
| 8,348,979 B2 | 1/2013 | McCormack |
| 8,541,383 B2 | 9/2013 | Gokaraju et al. |
| 8,815,280 B2 | 8/2014 | Rathmacher et al. |
| 2012/0053240 A1 | 3/2012 | Rathmacher et al. |
| 2013/0017283 A1 | 1/2013 | Zemel et al. |
| 2014/0148488 A1 | 5/2014 | Zemel et al. |

FOREIGN PATENT DOCUMENTS

CN        102762097 A        10/2012

OTHER PUBLICATIONS

Ostaszewski et al., "3 hydroxy 3 methylbutyrate and 2 oxoisocaproate affect body composition and cholesterol concentration in rabbits", "J Anim Physiol a Anim Nutr", Jan. 1, 1998, pp. 135-145, vol. 79.

Wilson et al., "Acute Timing Effects of HMB Supplementation on Serum Indices of Muscle Damage: 2939: Board #86 May 30 9:30 AM-11:00 AM", "Medicine & Science in Sports & Exercise", Jan. 1, 2009.

Wilson et al., "Acute and timing effects of beta-hydroxy-beta-methylbutyrate (HMB) on indirect markers of skeletal muscle damage", "Nutrition & Metabolism", Jan. 1, 2009, vol. 6, No. 6, Publisher: BioMed Central.

Wilson et al., "Beta-hydroxy-beta-methyl-butyrate blunts negative age-related changes in body composition, functionality and myofiber dimensions in rats", "Journal of the International Society of Sports Nutrition", Jan. 1, 2012, vol. 9, No. 18, Publisher: BioMed Central.

Cheng et al., "Beta Hydroxy beta Mehtyl butyrate increases fatty acid oxidation by muscle cells", Jan. 1, 1997, Publisher: FASEB.

Molfino et al., "Beta-hydroxy-beta-methylbutyrate supplementation in health and disease: a systematic review of randomized trials", "Amino Acids", Jan. 1, 2013, p. 12731292, vol. 45, Publisher: Springer.

Wilson et al., "Beta-hydroxy-beta-methylbutyrate (HMB) Decreases Body Fat in Middle Aged and Old Rats", "FASEB", Jan. 1, 2010, Publisher: FASEB.

Driskel, "B Hydroxy Methylbutyrate", "Sports Nutrition", Jan. 1, 2007.

Vukovich, "Body Composition in 70-Year-Old Adults Responds to Dietary b-Hydroxy-b-Methylbutyrate Similarly to That of Young Adults", "Nutrition and AgingResearch Communication", Jan. 1, 2001.

Flummer et al., "Body composition of piglets from sows fed the leucine metabolite B-hydroxy B-methyl butyrate in late gestation", "J Anim Sci", Jan. 1, 2012, pp. 442-444, vol. 90, Publisher: American Society of Animal Science.

Jowko et al., "Creatine and b-Hydroxy-b-Methylbutyrate (HMB) Additively Increase Lean Body Mass and Muscle Strength During a Weight-Training Program", "Applied Nutritional Investigation", Jan. 1, 2001, Publisher: Elsevier.

Kreider, "Dietary Supplements and the Promotion of Muscle Growth with Resistance Exercise", "Sports Med", Jan. 1, 1999, pp. 97-110, vol. 27, No. 2, Publisher: ADIS international.

Pittler et al., "Dietary supplements for body-weight reduction: a systematic review", "Am J Clin Nutr", Jan. 1, 2004, pp. 529-536, vol. 79, Publisher: American Society for Clinical Nutrition.

Szczesniak et al., "Dietary supplementation of b-hydroxy-b-methylbutyrate in animals a review", "Journal of Animal Physiology and Animal Nutrition", Jan. 1, 2015, pp. 405-417, vol. 99.

Marcora et al., "Dietary treatment of rheumatoid cachexia with b-hydroxy-b-methylbutyrate, glutamine and arginine: A randomised controlled trial", "Clinical Nutrition", Jan. 1, 2005, pp. 442-454, vol. 24, Publisher: Elsevier.

Cohen et al., "The effect of HMB and resistance training on changes in body compostiion during positive and negative energy balance a randomized double blind study", Jan. 1, 1998.

(Continued)

*Primary Examiner* — Sudhakar Katakam
(74) *Attorney, Agent, or Firm* — Davis, Brown, Koehn, Shors & Roberts, P.C.

(57) ABSTRACT

The present invention provides a composition comprising HMB. Methods of administering HMB to an animal are also described. HMB is administered to enhance or promote lipolysis, increase adipocyte fat oxidation, induce adipocyte and muscle mitochondrial biogenesis, increase energy expenditure, decrease total body weight and increase body fat loss.

16 Claims, 4 Drawing Sheets

(56) References Cited

OTHER PUBLICATIONS

Portal et al., "The effect of HMB supplementation on body composition, fitness, hormonal and inflammatory mediators in elite adolescent volleyball players: a prospective randomized, double-blind, placebo-controlled study", "Eur J Appl Physiol", Jan. 1, 2011, pp. 2261-2269, vol. 111.

Vukovich et al., "The effect b hydroxy b methylbutyrate on body composition changes measured by computerized tomography in older adults participating in an exercise program", Jan. 1, 1998, Publisher: FASEB.

Dunsmore et al., "Effects of 12 weeks of HMB free acid gel supplementation on muscle mass strength and power in resistance trained individuals", "Journal of the International Society of Sports Nutrition", Jan. 1, 2012, vol. 9, Publisher: BioMed Central.

Clark et al., "Effect of an Amino Acid Mixture Containing—Hydroxy-Methylbutyrate (HMB) In HIV Related Wasting.", Jan. 1, 1998, Publisher: Metabolic Technologies.

Stout et al., "Effect of calcium-hydroxy-methylbutyrate (CaHMB) with and without resistance training in men and women 65+ yrs: A randomized, double-blind pilot trial", "Experimental Gerontology", Jan. 1, 2013, pp. 1303-1310, vol. 48, Publisher: Elsevier.

Durkalec et al., "The Effect of b-Hydroxy-b-Methylbutyrate on Aerobic Capacity and Body Composition in Trained Athletes", "Journal of Strength and Conditioning Research", Jan. 1, 2016, vol. 30, No. 9, Publisher: National Strength and Conditioning Association.

Ostaszweski et al., "Effects of 3 Hydroxy 3 Methylbutyrate and 2 Oxoisocaproate on Body composition and cholesterol metabolism in rabbits", Jan. 1, 1995.

Vukovich et al., "The Effect of dietary b hydroxy b methylbutryate on strength gains and body composition changes in older adults", Jan. 1, 1997.

Nissen et al., "Effect of feeding HMB on body composition and strength of women", Jan. 1, 1997, vol. 11, Publisher: FASEB.

Cheng et al., "Effect of HMB of Fuel Utilization Membrane Stability and Cratine Kinase Content of Cultured Muscle Cells.", Jan. 1, 1998.

Wu et al., "Effect of beta-hydroxy-beta-methylbutyrate supplementation on muscle loss in older adults: A systematic review and meta-analysis", "Archives of Gerontology and Geriatrics", Jan. 1, 2015, pp. 168-175, vol. 61, Publisher: Elsevier.

Flakoll et al., "Effect of b-hydroxy-b-methylbutyrate, Arginine, and Lysine on Body Composition in Elderly Men and Women.", "J. Nutr. Health and Aging", Jan. 1, 2005, vol. 9, No. 2.

Qiao et al., "Effect of HMB calcium on growth blood parameteres and carcass qualities of broiler chickens", Jan. 1, 2013, Publisher: Poultry Science Association Inc.

Deutz et al., "Effect of b-hydroxy-b-methylbutyrate (HMB) on lean body mass during 10 days of bed rest in older adults", "Clinical Nutrition", Jan. 1, 2013, pp. 704-712, vol. 32, Publisher: Elsevier.

Nissen et al., "Effect of leucine metabolite b-hydroxy-b-methylbutyrate on muscle metabolism during resistance-exercise training", "American Physiological Society", Jan. 1, 1996.

Flakoll et al., "Effect of HMB Arginine and Lysine Supplementation on Strength Functionality, Body Composition, and Protein Metabolism in Elderly Women", "Applied Nutritional Investigation", Jan. 1, 2004, pp. 445-451, vol. 20, Publisher: Elsevier.

Ransone et al., "The Effect of b-Hydroxy b-Methylbutyrate on Muscular Strength and Body Composition in Collegiate Football Players", "Journal of Strength and Conditioning Research", Jan. 1, 2003, pp. 34-39, vol. 17, No. 1, Publisher: National Strength & Conditioning Association.

Vukovich, "Effect of HMB on the onset of blood lactate accumulation and VO2 peak in endurance trained cyclists", "Journal Strength and Conditioning Research", Jan. 1, 2001, pp. 491-497, vol. 45, No. 4.

Bruckbauer et al., "Effects of dairy consumption on SIRT1 and metabolic risk in humans", Jan. 1, 2011, vol. 25, Publisher: FASEB.

Coelho et al., "Effects of HMB supplementation on LDL cholesterol strenght and body compostion of patients with hypercholesterolemia", Jan. 1, 2001, p. S340, vol. 35, No. 5.

Kraemer et al., "Effects of Amino Acids Supplement on Physiological Adaptations to Resistance Training", Jan. 1, 2009, Publisher: American College of Sports Medicine.

Neighbors et al., "Effects of dietary hmb on body compoistion in collegiate football players", "Med&Sci in Sports and Exerc", Jan. 1, 2000, p. S60, vol. 32, No. 5.

Wilson et al., "The effects of 12 weeks of beta-hydroxy-beta-methylbutyrate free acid supplementation on muscle mass, strength, and power in resistance-trained individuals: a randomized, double-blind placebo-controlled study", "Eur J Appl Physiol", Jan. 1, 2014, pp. 1217-1227, vol. 114.

Townsend et al., "Effects of !-Hydroxy-!-methylbutyrate Free Acid Ingestion and Resistance Exercise on the Acute Endocrine Response", "International Journal of Endocrinology", Jan. 1, 2015, Publisher: Hindawi Publishing Corporation.

Wilson et al., "Effects of Amino Acids and their Metabolites on Aerobic and Anaerobic Sports", "Strength and Conditioning Journal", Jan. 1, 2012, Publisher: National Strength and Conditioning Association.

Breitman et al., "The Effects of an Amino Acid Supplement on Glucose Homeostasis, Inflammatory Markers, and Incretins after Laparoscopic Gastric Bypass", "American College of Surgeons", Jan. 1, 2011, Publisher: Elsevier.

Lambley et al., "Effects HMB on Aerobic Performance Components and body Composition in College Students", "Int. J of Sprot NUutrition and Exercise Metabolism", Jan. 1, 2007, pp. 56-69, vol. 17, Publisher: Human Kinetics.

Kreider et al., "Effects of Clacium HMB supplementation druing resistance training on markers of catabolism body composition and strength", "Physiology and Biochemistry", Jan. 1, 1999, pp. 503-509, vol. 20, Publisher: Georg Thieme Verlag Stuttgart.

Kreider et al., "Effects of Calcium B HMB supplementation with or without creatine during training on body composition alterations", Jan. 1, 1997, vol. 11, No. 3, Publisher: FASEB.

Bruckbauer et al., "Effects of dairy consumption on SIRT1 and mitochondrial biogenesis in adipocytes and muscle cells", "Nutrition & Metabolism", Jan. 1, 2011, vol. 8, No. 91, Publisher: BioMed Central.

Knitter, "Effects of b-hydroxy-b-methylbutyrate on muscle damage after a prolonged run", "J Appl Physiol", Jan. 1, 2000, pp. 1340-1344, vol. 89.

Wilson et al., "Effects of beta-hydroxy-beta-methylbutyrate (HMB) on exercise performance and body composition across varying levels of age, sex,and training experience: A review", "Nutrition & Metabolism", Jan. 1, 2008, vol. 5, No. 1, Publisher: BioMed Central.

Thomson et al., "Effects of Nine Weeks of b-Hydroxy-b-Methylbutyrate Supplementation on Strength and Body Composition in Resistance Trained Men", "Journal of Strength and Conditioning Research", Jan. 1, 2009, Publisher: National Strength and Conditioning Association.

Van Koevering et al., "Effects of HMB on performance and carcass quality of feelot steers", Jan. 1, 1994.

Kreider, "Effects of bHMB on Body Composition, Strength, and Sprint Performance", "Journal of Exercise Physiology", Jan. 1, 2000.

Escalante et al., "The effects of phosphatidic acid supplementation on strength, body composition, muscular endurance, power, agility, and vertical jump in resistance trained men", "Journal of the International Society of Sports Nutrition", Jan. 1, 2016, vol. 13, No. 24.

Knitter et al., "The effects of HMB on Muscle Damage and recoveru follwing a 20 km run", Jan. 1, 1998.

Hung et al., "Effect of b-Hydroxy-b-Methylbutyrate Supplementation During Energy Restriction in Female Judo Athletes", "J Exerc Sci Fit", Jan. 1, 2010, pp. 50-53, vol. 8, No. 1, Publisher: Elsevier.

Rathmacher et al., "Effect of Withdrawl of HMB glutamine and Arginine on Body Composition in AIDS patients", Jan. 1, 2000, p. s12, vol. 24, No. 1, Publisher: JPEN.

(56) References Cited

OTHER PUBLICATIONS

Nissen et al., "Effect of -Hydroxy-Methylbutyrate (HMB) Supplementation on Strength and Body Composition of Trained and Untrained Males Undergoing Intense Resistance Training", Jan. 1, 1996, Publisher: FASEB.

Durkalec et al., "The efficacy of a b-hydroxy-b-methylbutyrate supplementation on physical capacity, body composition and biochemical markers in elite rowers: a randomised, double-blind, placebo controlled crossover study", "Journal of the International Society of Sports Nutrition", Jan. 1, 2015, vol. 12, No. 31, Publisher: BioMed Central.

Fitschen et al., "Efficacy of b-hydroxy-b-methylbutyrate supplementation in elderly and clinical populations", "Nutrition", Jan. 1, 2013, pp. 26-36, vol. 29, Publisher: Elsevier.

Rahman et al., "Elderly Persons With ICU-Acquired Weakness: The Potential Role for -Hydroxy-Methylbutyrate (HMB) Supplementation?", "Journal of Parenteral and Enteral Nutrition", Jan. 1, 2014, pp. 567-575, vol. 38, No. 4, Publisher: aspen.

Cherniack et al., "Emerging therapies to treat frailty syndrome in the elderly", "Alternative Medicine Review", Nov. 3, 2007, vol. 12, No. 3.

Robinson et al., "High-intensity interval training and !-hydroxy-B-methylbutyric free acid improves aerobic powerand metabolic thresholds", Jan. 1, 2014, vol. 11, No. 16, Publisher: BioMed Central.

Kim et al., "!-Hydroxy-!-Methylbutyrate Did Not Enhance High Intensity Resistance Training-Induced Improvements in Myofiber Dimensions and Myogenic Capacity in Aged Female Rats", "Molecules and Cells", Nov. 1, 2012, Publisher: Springer.

Palisin et al., "HMB and its use in athletics", Jan. 1, 2005.

Park et al., "HMB attenuates muscle loss during sustained energy deficit induced by calorie restriction and endurance exercise", "Metabolism", Jan. 1, 2013, Publisher: Elsevier.

Portal, "Effect HMB supplementation on body composition fitness hormonal profile and muscle damage indices", "Journal of Pediatric Endocrinology and Metabolism", Jan. 1, 2010, pp. 641-650, vol. 23, Publisher: Freund Publishing House.

Gallagher et al., "b-hydroxy-b-methylbutyrate ingestion, Part I: effects on strength and fat free mass", "Medicine & Science in Sports & Exercise", Jan. 1, 2000, Publisher: American College of Sports Medicine.

Aversa et al., "b-Hydroxy-b-methylbutyrate (HMB) prevents dexamethasone-induced myotube atrophy", "Biochemical and Biophysical Research Communications", Jan. 1, 2012, pp. 739-743, vol. 423, Publisher: Elsevier.

Slater et al., "HMB supplementation and the promotion of muscle gorwth and strength", Jan. 1, 2000, Publisher: ADIS international.

Rowlands et al., "Effects of HMB supplenation during resistance training on strength body composition and muscle damage in trained and untrained young men: a meta analysis", "J of Strength and Conditioning Research", Jan. 1, 2009, pp. 836-846, vol. 23, No. 3, Publisher: National Srength and Conditioning Association.

Slater et al., "B Hydroxy B Methylbutyrate supplementation des not affect changes in strength or body compostion during resistance training in trained men", Jan. 1, 2001, Publisher: HKP.

Aversa et al., "-hydroxy-methylbutyrate (HMB) attenuates muscle and body weight loss in experimental cancer cachexia", "International Journal of Oncology", Jan. 1, 2011, pp. 713-720, vol. 38.

Thompson, "-Hydroxy-Methylbutyrate (HMB) supplementation of resistance trained men", "Asia Pacific Journal of Clinical Nutrition", Jan. 1, 2004, vol. 13.

Kendall et al., "B-hydroxy-B-methylbutyrate (HMB)Supplementation and Resistance Training (RT) May Improve Body Composition and Muscle Function in Healthy Elderly Men (6678 years): A 24 week study", "FASEB", Jan. 1, 2011, vol. 25, Publisher: FASEB.

Kim et al., "-Hydroxy-Methylbutyrate (HMB) Improves Body Composition and Myofiber Dimensions in Mice during Normal Physical Conditioning Not during Catabolic Conditions", "FASEB", Jan. 1, 2011, Publisher: FASEB.

Pimentel et al., "b-Hydroxy-b-methylbutyrate (HMb) supplementation stimulates skeletal muscle hypertrophy in rats via the mTOR pathway", "Nutrition and Metabolism", Jan. 1, 2011, vol. 8, Publisher: BioMed Central.

Pierson et al., "Injury Body Composition and Nitrogen Metabolism in the Surgical Patient", "Serono Symposia", Jan. 1, 2000, Publisher: Springer.

Lowery et al., "Interaction of Beta-Hydroxy-Beta-Methylbutyrate Free Acid and Adenosine Triphosphate on Muscle Mass, Strength, and Power in Resistance Trained Individuals", "Journal of Strength and Conditioning Research", Jan. 1, 2014, Publisher: National Strength and Conditioning Association.

Wilson et al., "International Society of Sports Nutrition Position Stand: beta-hydroxy-beta-methylbutyrate (HMB)", "Journal of the International Society of Sports Nutrition", Jan. 1, 2013, vol. 10, No. 6, Publisher: BiomedCentral.

Brioche et al., "Muscle wasting and aging: Experimental models, fatty infiltrations, and prevention", "Molecular Aspects of Medicine", Jan. 1, 2016, Publisher: Elsevier.

Clements et al., "Nutritional effect of oral supplement enriched in beta-hydroxy beta-methylbutyrate, glutamine and arginine on resting metabolic rate after laparoscopic gastric bypass", "Surg Endosc", Jan. 1, 2011, pp. 1376-1382, vol. 25, No. 5, Publisher: Springer.

Clark et al., "Nutritional Treatment for Acquired Immunodeficiency Virus-Associated Wasting Using B Hydroxy B MethylbutyrateGlutamine and Arginine a Randomized Double Blind Placebo Controlled Study", Jan. 1, 2000, vol. 2, No. 3, Publisher: ASPEN.

Nissen et al., "Nutritional role of the leucine metabolite B hydroxy B methylbutyrate HMB", Jan. 1, 1997, Publisher: Elsevier.

Panton et al., "Nutritional Supplementation of the Leucine Metabolite b-Hydroxy-b-Methylbutyrate (HMB) During Resistance Training", Jan. 1, 2000, pp. 734-739, vol. 16, Publisher: Elsevier.

Olveira et al., "Oral supplement enriched in HMB combined with pulmonary rehabilitation improves body composition and health related quality of life in patients with bronchiectasis (Prospective, Randomised Study)", "Clinical Nutrition", Jan. 1, 2016, pp. 1015-1022, vol. 35, Publisher: Elsevier.

Weitzel et al., "Performance-enhancing sports supplements: Role in critical care", "Crit Care Med", Jan. 1, 2009, vol. 37, No. 10.

Berk et al., "A randomized, double-blind, placebo-controlled trial of a !-hydroxyl !-methyl butyrate, glutamine, and arginine mixture for the treatment of cancer cachexia (RTOG 0122)", "Support Care Cancer", Jan. 1, 2008, pp. 1179-1188, vol. 16.

May et al., "Reversal of cancer-related wasting using oral supplementation with a combination of b-hydroxy-b-methylbutyrate, arginine, and glutamine", "The American Journal of Surgery", Jan. 1, 2002, pp. 471-479, vol. 183, Publisher: Excerpta Medica.

Stancliffe, "Role of BHydroxy Bmethylbutyrate HMB in leucine stimulation of muscle mitochondrial biogenesis", "FASEB journal", Jan. 1, 2012, Publisher: FASEB.

Stancliffe et al., "Role of mTOR and -hydroxy-methylbutyrate (HMB) in leucine stimulation of muscle mitochondrial biogenesis and fatty acid oxidation", "FASEB journal", Jan. 1, 2011, Publisher: FASEB.

Argiles et al., "Skeletal Muscle Regulates Metabolism via Interorgan Crosstalk: Roles in Health and Disease", "Jamda", Jan. 1, 2016, pp. 1-8, Publisher: Elsevier.

Wilson et al., "Supplementary Tables", Jan. 1, 2014.

Alon et al., "Supplementing with beta hydroxy beta methylbutyrate HMB to build and maintain muscle mass: a review", Jan. 1, 2002, pp. 139-152, vol. 111, No. 1-4, Publisher: PJD Publication.

Deutz et al., "Supplentary Data", Jan. 1, 2013.

Bruckbauer et al., "Synergistic effects of leucine and resveratrol on insulin sensitivity and fat metabolism in adipocytes and mice", "Nutrition & Metabolism", Jan. 1, 2012, vol. 9, No. 77, Publisher: BioMed Central.

Bruckbauer et al., "Synergistic effects of polyphenols and methylxanthines with leucine on AMPK/Sirtuin-Mediated Metabolism in muscle cells and adipocytes", Feb. 1, 2014, vol. 9, No. 2, Publisher: PLOS one.

(56) References Cited

OTHER PUBLICATIONS

Bruckbauer et al., "Synergistic effects of metformin, resveratrol, and hydroxymethylbutyrate on insulin sensitivity", "Diabetes, Metabolic Syndrome and Obesity: Targets and Therapy", Jan. 1, 2013, vol. 6, Publisher: Dovepress.

Albert et al., "Usefulness of !-hydroxy-!-methylbutyrate (HMB) supplementation in different sports: an update and practical implications", Jan. 1, 2015.

Fuller et al., "Vitamin D Status Affects Strength Gains in Older Adults Supplemented With a Combination of b-Hydroxy-BBethylbutyrate Arginine and Lysine: A Cohort Study", "Journal of Parenteral and Enteral Nutrition", Nov. 1, 2011, vol. 35, No. 6, Publisher: SAGE.

Baier et al., "Year-long Changes in Protein Metabolism in Elderly Men and Women Supplemented With a Nutrition Cocktail of B-Hydroxy-methylbutyrate (HMB),L-Arginine, and L-Lysine", "Journal of Parenteral and Enteral Nutrition", Jan. 1, 2009, vol. 33, No. 1.

Ferreira et al., "The Effects of Supplementation of HMB on Inflammatory Markers in High Performance Athletes", "Journal of Exercise Physiology", Feb. 1, 2013, vol. 16, No. 1.

\* cited by examiner

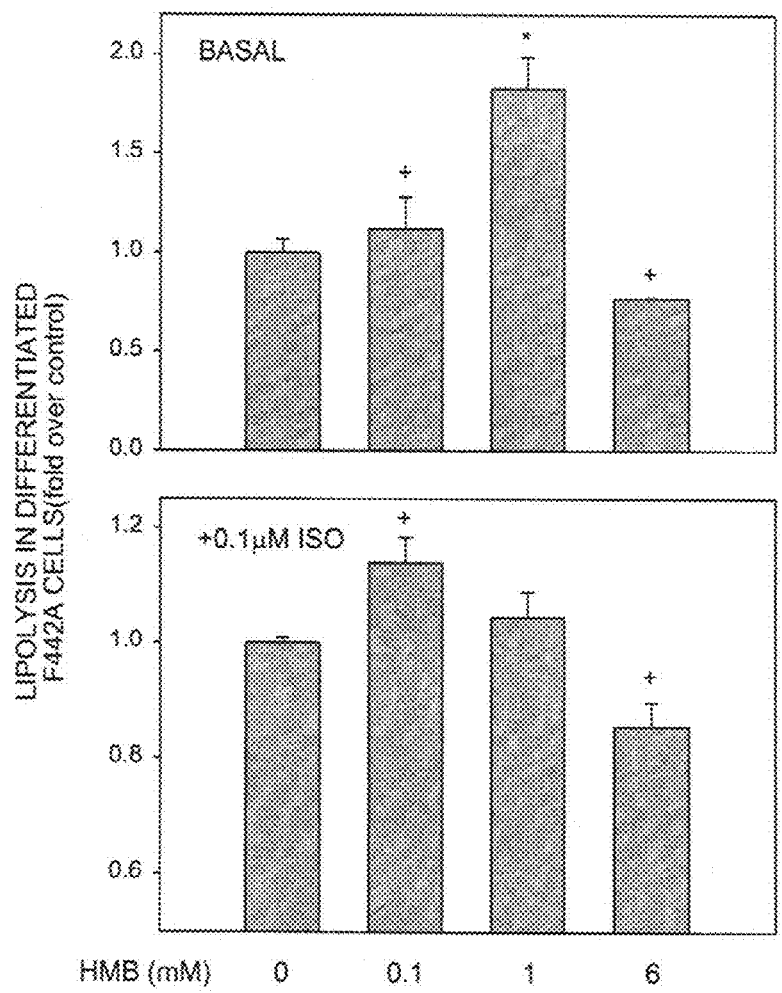
Figure 1: Lipolysis in 3T3-F442A Adipocytes

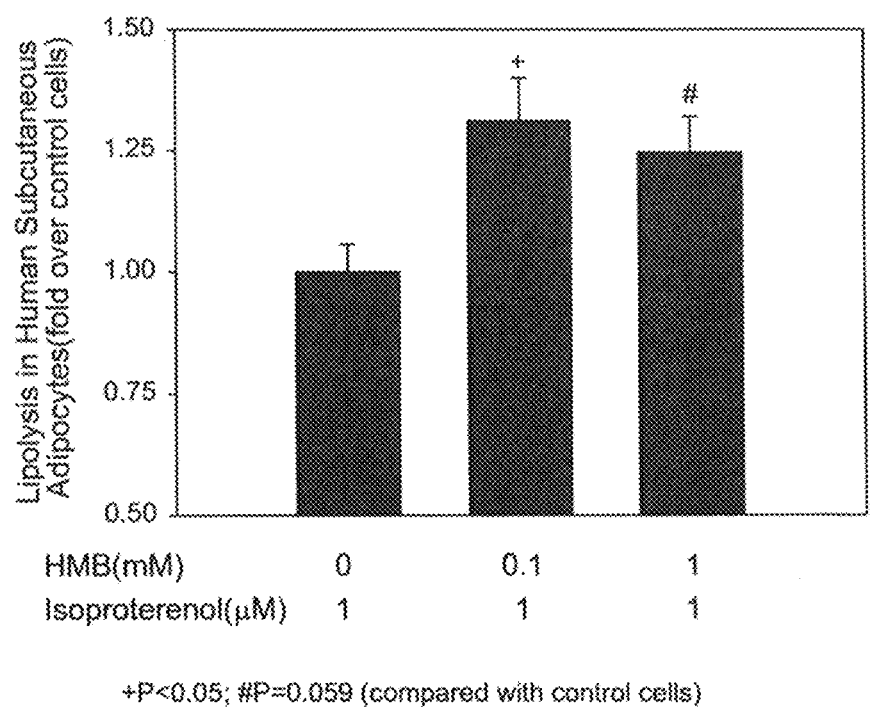
Figure 2. Lipolysis in Human Subcutaneous Adipocytes

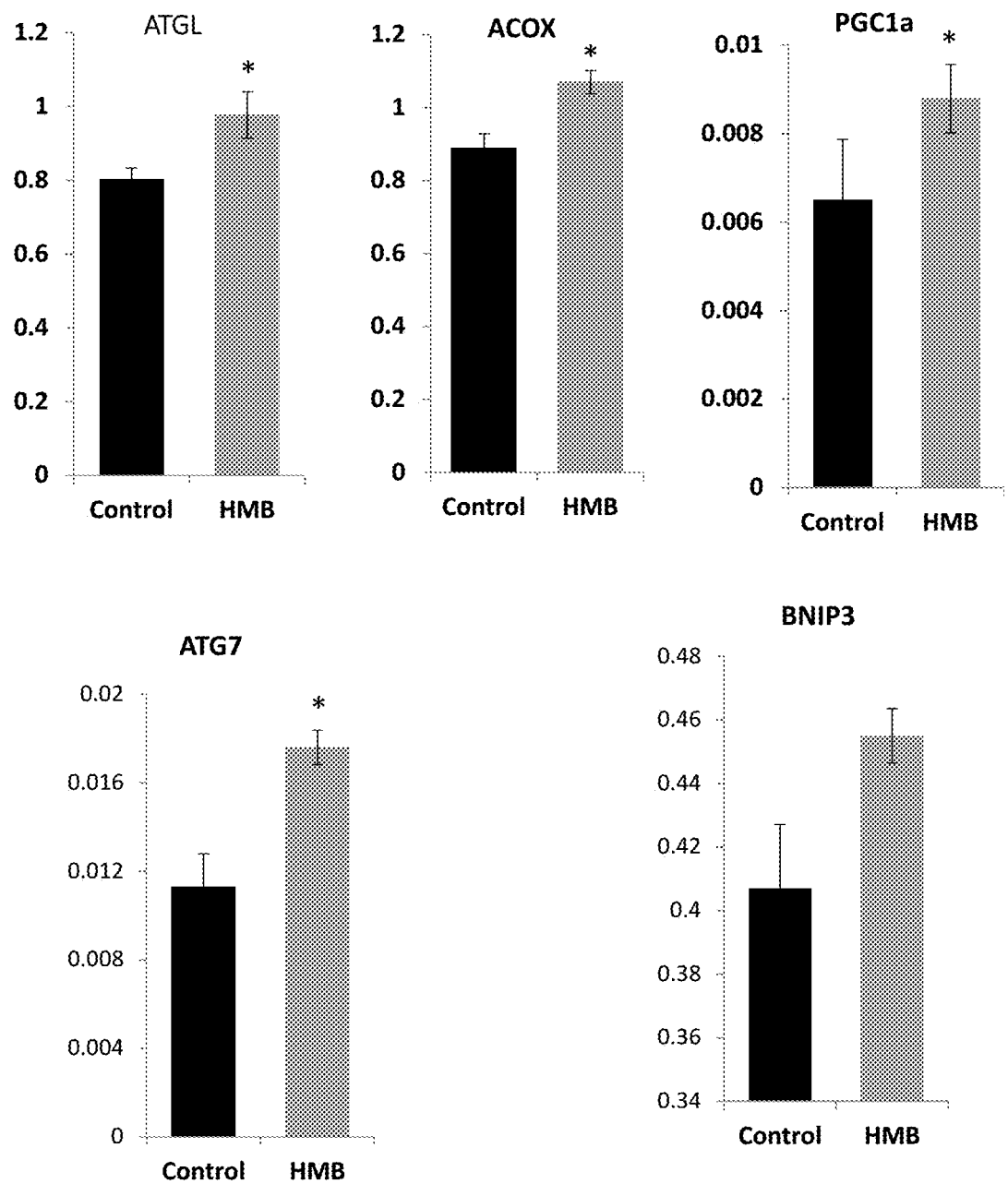
Figure 3: Gene Expression

Figure 4: 48h HMB Treatment increases beta adrenergic stimulated lipolysis in OP9 adipocytes
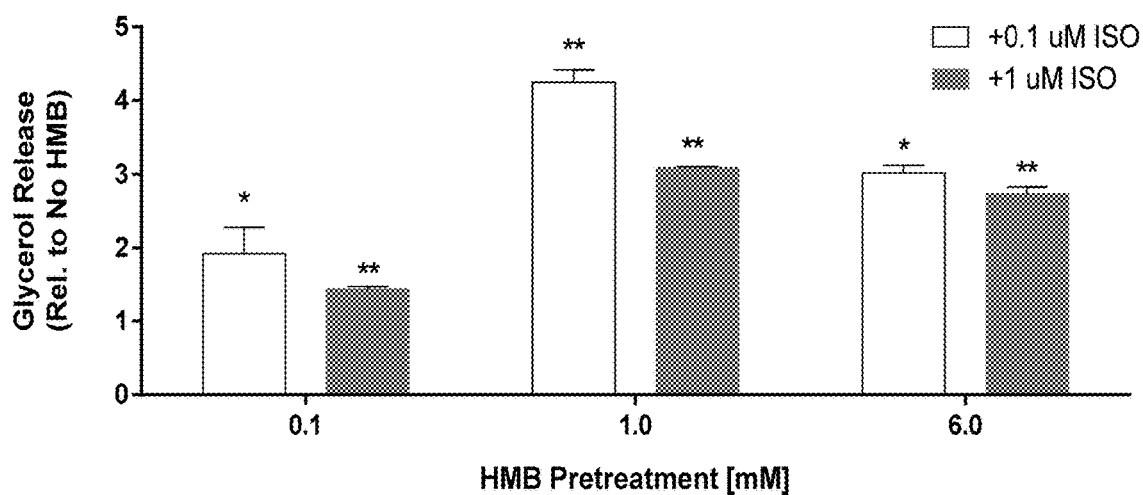
Figure 5:   HMB pretreatment increases basal lipolysis
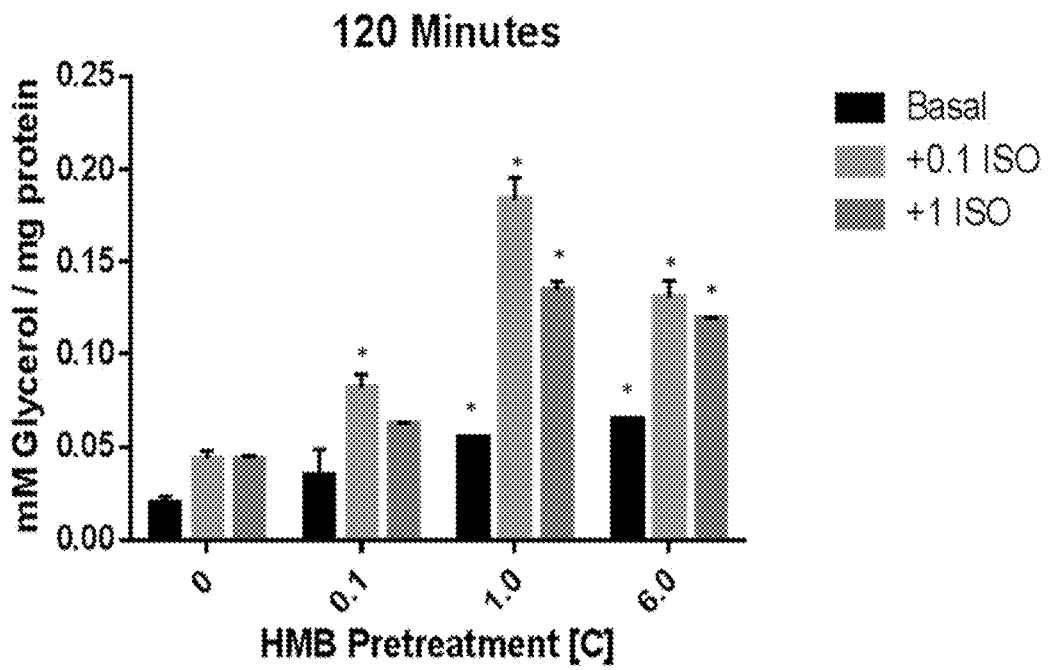

COMPOSITIONS AND METHODS OF USE OF BETA-HYDROXY-BETA-METHYLBUTYRATE (HMB) FOR DECREASING FAT MASS

This application claims priority to U.S. Provisional Patent Application No. 62/169,334 filed Jun. 1, 2015 and herein incorporates the provisional application by reference. This application is a divisional of U.S. patent application Ser. No. 15/170,329 filed Jun. 1, 2016.

BACKGROUND OF THE INVENTION

1. Field

The present invention relates to a composition comprising β-hydroxy-β-methylbutyrate (HMB) and methods of using HMB to enhance lipolysis, increase body fat loss, reduce adipocyte size, increase adipocyte fatty acid metabolism, reduce total body weight, and lower adipocyte inflammation.

2. Background

The high prevalence of obesity is a major public health and economic burden driving an urgent need for effective nutritional management of obesity and obesity-associated comorbidities. Recently, chronic inflammation has been recognized as a contributing factor in the pathogenesis of many metabolic diseases, originating, in part, from adipose tissue. Specifically, adipocyte hypertrophy drives an inflammatory gene profile associated with metabolic dysfunction. Currently, there is a national priority to develop effective tools for the management of obesity and adipose tissue inflammation, including nutritional products for the control of appetite and maintenance of optimal body composition during weight loss. However, the science behind weight loss products has thus far been primarily based solely upon caloric restriction, and not the maintenance of lean tissue versus fat tissue loss. The ideal weight loss program would drive preferential loss of adipose tissue over muscle tissue. Improvements in adipocyte metabolism lead to reductions in adipocyte size, oxidative stress, and inflammation, and promotion of cardio-metabolic health.

The increase in the prevalence of obesity is a health crisis of extraordinary magnitude, and it is projected that by 2030, approximately 50% of the adult population will be obese. Obesity is linked to type 2 diabetes (T2D), cardiovascular disease (CVD), hypertension, and many cancers. In addition to devastating impact on quality of life, obesity and associated co-morbidities increase average annual medical costs per person by $2,741 (2005 dollars) compared to costs for normal weight people, including 46% increased inpatient costs, 27% more outpatient costs, and 80% increased spending on prescription drugs. Additionally, costs attributable to lost productivity for full time employees are estimated to be $42.8 billion annually.

Branch chain amino acids, and leucine in particular, are recognized as key regulators of protein metabolism. Several studies have shown that β-hydroxy-β-methylbutyrate (HMB), a natural metabolite of leucine, is more effective than leucine leading to reductions in muscle protein breakdown and promoting muscle protein synthesis, translating into increased lean body mass and improved muscle function in both young and older adults, during health and disease.

A leucine-deficient diet has been demonstrated to cause a dramatic reduction in abdominal fat mass (Cheng et al., *Diabetes*, 2010 January, 59(1): 17-25), making the findings of the present invention surprising and unexpected.

HMB

Alpha-ketoisocaproate (KIC) is the first major and active metabolite of leucine. A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting.

The use of HMB to suppress proteolysis originates from the observations that leucine has protein-sparing characteristics. The essential amino acid leucine can either be used for protein synthesis or transaminated to the α-ketoacid (α-ketoisocaproate, KIC). In one pathway, KIC can be oxidized to HMB and this account for approximately 5% of leucine oxidation. HMB is superior to leucine in enhancing muscle mass and strength. The optimal effects of HMB can be achieved at 3.0 grams per day when given as calcium salt of HMB, or 0.038 g·kg of body weigh$^{-1}$-day, while those of leucine require over 30.0 grams per day.

Once produced or ingested, HMB appears to have two fates. The first fate is simple excretion in urine. After HMB is fed, urine concentrations increase, resulting in an approximate 20-50% loss of HMB to urine. Another fate relates to the activation of HMB to HMB-CoA. Once converted to HMB-CoA, further metabolism may occur, either dehydration of HMB-CoA to MC-CoA, or a direct conversion of HMB-CoA to HMG-CoA, which provides substrates for intracellular cholesterol synthesis. Several studies have shown that HMB is incorporated into the cholesterol synthetic pathway and could be a source for new cell membranes that are used for the regeneration of damaged cell membranes. Human studies have shown that muscle damage following intense exercise, measured by elevated plasma CPK (creatine phosphokinase), is reduced with HMB supplementation within the first 48 hrs. The protective effect of HMB lasts up to three weeks with continued daily use. Numerous studies have shown an effective dose of HMB to be 3.0 grams per day as CaHMB (calcium HMB) (~38 mg·/kg body weight$^{-1}$ day$^{-1}$). This dosage increases muscle mass and strength gains associated with resistance training, while minimizing muscle damage associated with strenuous exercise. HMB has been tested for safety, showing no side effects in healthy young or old adults. HMB in combination with L-arginine and L-glutamine has also been shown to be safe when supplemented to AIDS and cancer patients.

Recently, HMB free acid, a new delivery form of HMB, has been developed. This new delivery form has been shown to be absorbed quicker and have greater tissue clearance than CaHMB. The new delivery form is described in U.S. Patent Publication Serial No. 20120053240 which is herein incorporated by reference in its entirety.

Current evidence suggests that HMB acts by speeding regenerative capacity of skeletal muscle following high intensity or prolonged exercise. When training and/or diet are controlled, HMB can lower indices of skeletal muscle damage and protein breakdown in a dose-dependent fashion.

Recently, HMB in a free acid form (HMB-FA) has been developed with improved bioavailability. Initial studies have shown that this form of HMB supplementation results in approximately double the plasma levels of HMB in about one-quarter the time after administration when compared with the presently available form, calcium HMB. Further, HMB-FA given 30 minutes prior to an acute bout of high volume resistance training was able to attenuate indices of muscle damage and improve perceived recovery in resistance trained athletes. Moreover, acute ingestion of 2.4 grams of HMB-FA increases skeletal muscle protein synthesis and decreases protein breakdown by +70% and −56% respectively.

The effects of HMB on muscle are well documented. It is known that HMB supplementation leads to increased muscle mass and strength and can result in aerobic improvement. While increases in lean muscle mass change overall body composition, it has been assumed that HMB only affects muscle cells to increase muscle mass which in turn changes body composition. Prior to the discoveries described in the present invention, it was not known that HMB had any direct effect on adipocytes and adipose tissue.

Most weight loss is initiated by hypocaloric diets. This weight loss comprises losses in both fat mass and lean body mass (i.e. skeletal muscle), in a ratio that is estimated to be 2:1. Exercise results in weight loss that is primarily accounted for by fat mass losses, with minor or significant increases in muscle mass. A significant number of the body mass changes that occur in exercise are now thought to be mediated by the classical (beneficial) pathway of IL-6. Surprisingly, HMB has a similar effect to that of exercise but without the exercise being a variable; fat mass loss is seen even in the absence of exercise.

The present invention comprises a composition of HMB and methods of use of HMB to result in enhanced lipolysis, increased adipocyte fat oxidation, induced adipocyte and muscle mitochondrial biogenesis, increased energy expenditure, reductions in body weight and increased body fat loss. HMB can thus be used for improvement of body contour, as defined by enhanced lean body mass in conjunction with decreased fat mass. This can result in a reduction of total body weight. These effects are seen with or without caloric restriction and without requiring exercise.

Use of HMB to increase lipolysis and/or decrease fat mass also decreases the associated morbidities of obesity, such as Type 2 diabetes, cardiovascular disease, chronic inflammation, cancer and other associated comorbidities.

In addition to administering HMB to humans to result in the above-described effects on adipocytes, adipose tissue and fat loss, the present invention includes administering a composition of HMB to animals with the same effects on adipocytes, adipose tissue and fat loss. There is a high rate of obesity among companion animals; an estimated 54% of cats and dogs in the United States are overweight or obese. Thus a need exists for compositions and methods of use of these compositions to result in fat loss in animals.

SUMMARY OF THE INVENTION

One object of the present invention is to provide a composition for use in fat loss and/or reductions in body weight.

A further object of the present invention is to provide a composition for use in increasing adipocyte and/or adipose tissue fat oxidation.

Another object of the present invention is to provide a composition to induce adipocyte and muscle mitochondrial biogenesis.

An additional object of the present invention is to provide a composition to increase energy expenditure.

Additionally, an object of the present invention is to provide a composition for use in enhancing lipolysis.

Another object of the present invention is to provide methods of administering a composition for use in fat loss.

An additional object of the present invention is to provide methods of administering a composition for increasing adipocyte and muscle fat oxidation.

Another object of the present invention is to provide methods of administering a composition for use in inducing adipocyte and muscle mitochondrial biogenesis.

A further object of the present invention is to provide methods of administering a composition for use in increasing energy expenditure.

Additionally, an object of the present invention is to provide methods of administering a composition for use in fat loss.

Another object of the present invention is to provide methods of administering a composition for use in reductions in body weight.

A further object of the present invention is to provide methods of administering a composition for use in enhancing lipolysis.

An additional object of the present invention is to provide methods of administering a composition for use in decreasing the associated morbidities of obesity, including Type 2 diabetes, cardiovascular disease, chronic inflammation, cancer and other associated comorbidities.

These and other objects of the present invention will become apparent to those skilled in the art upon reference to the following specification, drawings, and claims.

The present invention intends to overcome the difficulties encountered heretofore. To that end, a composition comprising HMB is provided. The composition is administered to a subject in need thereof. All methods comprise administering to the animal, HMB. The subjects included in this invention include humans and non-human mammals.

BRIEF DESCRIPTION OF THE DRAWINGS

FIG. 1 is a graph showing lipolysis in 3T3-F442A Adipocytes.

FIG. 2 is a graph showing lipolysis in Human Subcutaneous Adipocytes.

FIG. 3 shows gene expression.

FIG. 4 is a graph showing lipolysis in OP9 Adipocytes.

FIG. 5 is a graph showing basal lipolysis.

DETAILED DESCRIPTION OF THE INVENTION

It has been surprisingly and unexpectedly discovered that HMB affects adipocytes and adipose tissue. The present invention comprises a composition of HMB and methods of use of HMB to result in increased enhanced lipolysis, adipocyte fat oxidation, induced adipocyte and muscle mitochondrial biogenesis, increased energy expenditure, reductions in body weight, and increased fat loss. These effects are seen with or without caloric restriction and without requiring exercise, although exercise can be conducted in conjunction with supplementation with the composition and methods of the present invention.

This composition can be used on all age groups seeking fat loss. This composition can also be used in humans and non-human mammals, including but not limited to companion animals.

HMB

β-hydroxy-β-methylbutyric acid, or β-hydroxy-isovaleric acid, can be represented in its free acid form as $(CH_3)_2(OH)CCH_2COOH$. The term "HMB" refers to the compound having the foregoing chemical formula, in both its free acid and salt forms, and derivatives thereof. While any form of HMB can be used within the context of the present invention, preferably HMB is selected from the group comprising a free acid, a salt, an ester, and a lactone. HMB esters include methyl and ethyl esters. HMB lactones include isovalaryl lactone. HMB salts include sodium salt, potassium salt, chromium salt, calcium salt, magnesium salt, alkali metal salts, and earth metal salts.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to a salt. For example, HMB can be prepared as its calcium salt by a procedure similar to that of Coffman et al. (1958) in which the free acid of HMB is neutralized with calcium hydroxide and recovered by crystallization from an aqueous ethanol solution. The calcium salt and free-acid forms of HMB are commercially available from Metabolic Technologies, Ames, Iowa.

Calcium β-hydroxy-β-methylbutyrate (HMB) Supplementation

More than 2 decades ago, the calcium salt of HMB was developed as a nutritional supplement for humans. Numerous studies have shown that CaHMB supplementation improves muscle mass and strength gains in conjunction with resistance-exercise training, and attenuates loss of muscle mass in conditions such as cancer and AIDS. Nissen and Sharp performed a meta-analysis of supplements used in conjunction with resistance training and found that HMB was one of only two supplements that had clinical studies showing significant increases in strength and lean mass with resistance training. Studies have shown that 38 mg of CaHMB per kg of body weight per day appears to be an efficacious dosage for an average person.

In addition to strength and muscle mass gains, CaHMB supplementation also decreases indicators of muscle damage and muscle protein degradation. Human studies have shown that muscle damage following intense exercise, measured by elevated plasma CPK (creatine phosphokinase), is reduced with HMB supplementation. The protective effect of HMB has been shown to manifest itself for at least three weeks with continued daily use. In vitro studies in isolated rat muscle show that HMB is a potent inhibitor of muscle proteolysis especially during periods of stress. These findings have been confirmed in humans; for example, HMB inhibits muscle proteolysis in subjects engaging in resistance training.

The molecular mechanisms by which HMB decreases protein breakdown and increases protein synthesis have been reported. Eley et al conducted in vitro studies which have shown that HMB stimulates protein synthesis through mTOR phosphorylation. Other studies have shown HMB decreases proteolysis through attenuation of the induction of the ubiquitin-proteosome proteolytic pathway when muscle protein catabolism is stimulated by proteolysis inducing factor (PIF), lipopolysaccharide (LPS), and angiotensin II. Still other studies have demonstrated that HMB also attenuates the activation of caspases-3 and -8 proteases. Taken together these studies indicate that HMB supplementation results in increased lean mass and the accompanying strength gains through a combination of decreased proteolysis and increased protein synthesis.

HMB Free Acid Form

In most instances, the HMB utilized in clinical studies and marketed as an ergogenic aid has been in the calcium salt form. Recent advances have allowed the HMB to be manufactured in a free acid form for use as a nutritional supplement. Recently, a new free acid form of HMB was developed, which was shown to be more rapidly absorbed than CaHMB, resulting in quicker and higher peak serum HMB levels and improved serum clearance to the tissues.

HMB free acid may therefore be a more efficacious method of administering HMB than the calcium salt form, particularly when administered directly preceding intense exercise. HMB free acid initiated 30 min prior to an acute bout of exercise was more efficacious in attenuating muscle damage and ameliorating inflammatory response than CaHMB. One of ordinary skill in the art, however, will recognize that this current invention encompasses HMB in any form.

HMB in any form may be incorporated into the delivery and/or administration form in a fashion so as to result in a typical dosage range of about 0.5 grams HMB to about 30 grams HMB.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, proteins, peptides, carbohydrates, fats, sugars, minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water.

The composition of the dietary supplement may be a powder, a gel, a liquid or may be tabulated or encapsulated.

Although any suitable pharmaceutical medium comprising the composition can be utilized within the context of the present invention, preferably, the composition is combined with a suitable pharmaceutical carrier, such as dextrose or sucrose.

The composition can be administered orally as a tablet, capsule, softgel, pill, sublingual gel, or as a liquid. The composition can be administered with other components, such as protein, free form amino acids, carbohydrates, sugars, vitamins (such as vitamin D, vitamin C, vitamin $B_{12}$, vitamin $B_6$, vitamin E, and/or vitamin K) and/or minerals.

Furthermore, the composition of the pharmaceutical medium can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids, peptides, proteins and/or lipids. The amounts of the composition to be administered intravenously can be similar to levels used in oral administration. Intravenous infusion may be more controlled and accurate than oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). HMB can be administered over an extended period of time, such as weeks, months or years.

Any suitable dose of HMB can be used within the context of the present invention. Methods of calculating proper doses are well known in the art.

In general, an amount of HMB in the levels sufficient to result in enhanced lipolysis, increased adipocyte fat oxidation, induced adipocyte and muscle mitochondrial biogenesis, increased energy expenditure and increased fat loss. These effects are seen with or without caloric restriction and without requiring exercise.

EXPERIMENTAL EXAMPLES

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

Lipolysis in 3T3-F442A Adipocytes

Methods. Murine 3T3-F442A preadipocytes were grown until confluence. After confluence, 3T3-F442A cells were allowed to differentiate into adipocytes and become filled with triglycerides. Lipolysis was assessed as glycerol release from 3T3-F442A adipocytes in well plates. Adipocyte monolayers were incubated with Krebs-Ringer buffer containing Hepes (KRH), supplemented with 2% fatty acid-free BSA, 5 mM glucose, ADA and PIA. In addition, cells were treated with β-hydroxy-β-methylbutyrate (HMB) at either 0 (control), 0.1, 1, or 6 mM concentrations. Cells were incubated in the absence (Basal) or in the presence of 0.1 μM isoproterenol for 1 hour. Aliquots of the incubation medium were removed and frozen until glycerol determination. Glycerol was measured by a commercial enzymatic method. Data were presented as the fold increase over control.

Results. The effect of HMB on lipolysis in differentiated 3T3-F442A adipocytes is shown in FIG. 1. Under basal conditions, HMB at 0.1 and 1 mM concentrations increased lipolysis above control, but HMB decreased lipolysis at the 6.0 mM included level. In response to the isoproterenol stimulation, 0.1 mM HMB increased lipolysis but HMB decreased lipolysis at the 6.0 mM included level. These data indicate that HMB can regulate the triglyceride content of adipocytes by increasing the lipolytic activity in a dose-responsive manner in both a basal condition and when stimulated.

Lipolysis in Human Subcutaneous Adipocytes

Methods. Human subcutaneous adipocytes were obtained from donors and incubated in vitro. Lipolysis was assessed as glycerol release in well plates. Adipocyte were incubated with Krebs-Ringer buffer containing Hepes (KRH), supplemented with 4% fatty acid-free BSA, 5 mM glucose, ADA and PIA. In addition, cells were treated with β-hydroxy-β-methylbutyrate (HMB) at either 0 (control), 0.1, or 1 mM concentrations in the presence of 1.0 μM isoproterenol for 2 hours. Aliquots of the incubation medium were removed and frozen until glycerol determination. Glycerol was measured by a commercial enzymatic method. Data were presented as the fold increase over control.

Results. The effect of HMB on lipolysis in human subcutaneous adipocytes is shown in FIG. 2. In response to the isoproterenol stimulation, 0.1 and 1 mM HMB increased lipolysis above that of control supplemented adipocytes. These data indicate that HMB can regulate the triglyceride content of adipocytes by increasing the lipolytic activity. These findings demonstrate that HMB may be used to reduce fat content in humans and can accelerate weight loss in obese humans.

Effect of HMB on Gene Expression in Differentiated Adipocytes

SGBS human pre-adipocytes were differentiated into adipocytes and treated with 1 mM HMB for 4 days. The human Simpson-Golabi-Behmel syndrome (SGBS) preadipocyte cell strain cells originate from an adipose tissue specimen of a patient with GSBS. Microarrays (mRNAs) were performed. The data show significant elevation (2.53 fold) in the canonical (classic) IL6 signaling pathway, which has recently been shown to be anti-inflammatory and protective. Similarly, cytokine receptor interaction and calcium signaling pathways are also elevated as measured by mRNAs. Table 1 describes the results.

TABLE 1

| Pathway: | Effect | p |
| --- | --- | --- |
| IL6 signaling | 2.53 | 0.011 |
| Cytokine, cytokine receptor interaction | 2.37 | 0.018 |
| Calcium signaling pathway | 2.09 | 0.037 |

Gene Expression

Differentiated adipocytes were incubated for 4 days with 1 mM of HMB. RNA was extracted and gene expression was determined by qPCR. Gene expression for ATGL, ACOX, PGC1a, ATG7 and BNIP3 were analyzed. ATGL is an adipose triglyceride lipase (ATGL) and was found to play a major role in catalyzing the initial step in triglyceride hydrolysis. ATGL is highly expressed in adipose tissue of humans and mice. ACOX1, or acyl-CoA oxidase 1 is the first enzyme involved in peroxisomal fatty acid oxidation. This occurs when the fatty acid chains are too long to be handled by the mitochondria. The high-potential electrons generated are transferred to $O_2 \rightarrow H_2O_2$ (+heat) which in the presence of catalase$\rightarrow H_2O$ and $O_2$. PGC1α is a key regulator of energy metabolism and is found to be very important in the development of brown adipose tissue which is the high energy yielding adipose tissue. Autophagy-related protein 7 (ATG7) regulates fat mass. Knocking ATG7 down will result in abnormal non-functional adipose tissue. Elevated levels increase tissue recycling. BNIP3 is another autophagy-related protein like ATG7 that appears to be significant. The gene expression results appear in FIG. 3.

Phosphokinase Protein Array of SGBS Adipocytes Treated with HMB

This approach was used to determine in non-biased way changes in protein phosphorylation that are known to influence activity of important signaling proteins. Differentiated human adipocytes were treated for 4 days with or without HMB (1 mM).

Shown are only the significant increases above untreated cells in phosphorylation of the listed protein at the indicated phosphorylation site(s). Protein arrays were performed and Table 2 shows that the phosphorylated proteins that up-regulated following incubation of differentiated adipocytes with HMB and Table 3 shows the proteins that were down-regulated

TABLE 2

Human adipocyte genes up-regulated with HMB

| Fold Change with HMB | Protein | Phosphor-ylation-Site | Comments |
|---|---|---|---|
| 1.255 | GSK-3a/b | S21/S9 | Glycogen Synthase Kinase. Phosphorylated by insulin |
| 1.233 | CREB | S133 | Enhances adipogenesis |
| 1.335 | Lyn | Y397 | Src kinase (lipid metabolism) |
| 1.400 | Fyn | Y420 | Src kinase (regulates FA metabolism). |
| 1.224 | Yes | Y426 | Src kinase (regulates endocytosis, e.g. EGFR) |
| 1.262 | FGR | Y412 | Src kinase, negative on cell adhesion/migration |

TABLE 3

Human adipocyte genes down-regulated with HMB

| Fold Change with HMB | Protein | Phosphor-ylation-Site | Comments |
|---|---|---|---|
| 0.804 | STAT5a/b | Y694/Y699 | Activated by IL7, FAS |
| 0.665 | Stat3 | Y705 | Activated by IL6, leptin |
| 0.732 | RSK1/2/3 | S380/S386/S377 | Highly conserved Ser/Thr kinase, regulates diverse cellular processes: growth, motility, survival etc. Effector of (ERK)/mitogen-activated protein kinase (MAPK) signaling. Might inhibits glucose transport |
| 0.621 | p53 | S15 | Regulates cell cycle. Enhances adipose differentiation. |
| 0.834 | P53 | S46 | Regulates cell cycle. Enhances adipose differentiation. |
| 0.711 | AKT1/2/3 | S473 | AKT mediates many insulin effects and effects of other regulators (e.g. growth factors) on cell growth etc. S473 is 1 of 2 activation sites. S473 phosphorylation is induced by insulin via PDK1 and by Focal Adhesion Kinase (FAK) in response to extracellular signals (from matrix, cell interaction). |

One notable finding is that of a decrease in Stat 3 which is involved in the beneficial pathway of IL-6. In addition, a decrease in AKT 1/2/3 transcript, a protein that is phosphorylated at serine 473 and is intimately involved with the mTOR pathway, was seen. This contrasts with no change in AKT1/2/3 which is at Threonine 308 and is involved in the insulin signaling pathway. The SRC kinases, Fyn, yes and lyn are involved in fatty acid metabolism.

These studies were conducted in the absence of electrical stimuli simulating exercise, demonstrating that HMB supplementation is effective for fat loss even in the absence of exercise.

HMB Regulation of Basal and Isoproterenol Stimulated Lipolysis in Differentiated Adipocytes.

As noted above, an increase in expression of ATGL in cells treated with HMB was observed, so the effect of HMB treatment on basal and isoproterenol stimulated lipolysis was determined directly in cultured adipocytes. The protocol of Viswanadha and Londos was used for optimization of conditions for measuring lipolysis in murine primary adipoctyes (J. Lipid Res. 2006. 47: 1859-1864) that include treatment with adenosine deaminase (ADA) to remove endogenous adenosine and then addition of ADA resistant PIA (phenylisopropyl-adenosine).

The following treatment strategies were tested: HMB doses of 0.1, 1 and 6 mM; 2 concentrations of the beta-adrenergic agonist isoproterenol 0.1 and 1 uM, and short term (immediately before lipolysis assay) vs. long term (48 h) HMB treatment (n=4 per treatment). Op9 adipocytes were used as SGBS cells take a long time (several weeks) to differentiate making them inconvenient to use.

Cells were pre-treated with varying concentrations of HMB in OP9 growth medium for 48 hrs. Following pre-treatment, cells were washed and incubated with Isoproterenol (0.1 or 1.0 uM) in lipolysis buffer: Krebs ringer bicarbonate (KRB) with 4% BSA. The medium also contained adenosine deaminase (ADA) and phenyl-isopropyl-adenosine (PIA) for 2 hrs at 37° C. ADA was added to remove endogenous adenosine and PIA, which is resistant to ADA, was used to have low standardized basal lipolysis. Following treatment, media was assayed for glycerol content and cells were lysed with RIPA buffer to determine protein concentration, *p<0.05, ** p<0.01. N=4.

The results are shown in FIGS. 4 and 5:

a) Pre-treatment with HMB for 48 h dramatically (2-4 fold) enhanced isoproterenol-stimulated lipolysis in differentiated OP9 adipocytes (FIG. 4)

b) At 0.1 mM HMB, lipolysis was enhanced by 2 fold in response to 0.1 uM isoproterenol (FIGS. 4 and 5).

c) At 1 mM HMB, a 4-fold increase over no HMB was observed at 0.1 uM isoproterenol (FIGS. 4 and 5).

d) At 6 mM the response to 0.1 uM isoproterenol was enhanced 3-fold so the dose of 1 mM HMB appears optimal (FIG. 4).

e) Higher concentrations of isoproterenol reduced maximal lipolysis as would be predicted by desensitization of adrenergic receptors (FIG. 5).

f) Under the above conditions used for the lipolysis assay, i.e. addition of ADA followed by PIA to clamp basal lipolysis at low level, HMB pretreatment also increased basal lipolysis about 2-fold (FIG. 4).

These experimental examples demonstrate that HMB has a direct effect on adipocytes and adipose tissue and show that supplementation with HMB can be used for fat loss.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

The invention claimed is:

1. A method of increasing intracellular lipolysis in adipose tissue of an animal in need thereof comprising administering to said animal a composition of from about 0.5 g to about 30 g of β-hydroxy-β-methylbutyric acid (HMB) thereby increasing lipolysis in the adipose tissue of the animal.

2. The method of claim 1, wherein said HMB is selected from the group consisting of its free acid form, its salt, its ester, and its lactone.

3. The method of claim 2, wherein said salt is selected from the group consisting of a sodium salt, a potassium salt, a magnesium salt, a chromium salt and a calcium salt.

4. The method of claim 1, wherein the animal is not participating in an exercise program.

5. A method of inducing fat loss by increasing intracellular lipolysis in an animal in need thereof comprising administering to the animal a composition of from about 0.5 g to about 30 g of β-hydroxy-β-methylbutyric acid (HMB) thereby inducing fat loss by increasing intracellular lipolysis.

6. The method of claim 5, wherein said HMB is selected from the group consisting of its free acid form, its salt, its ester, and its lactone.

7. The method of claim 6, wherein said salt is selected from the group consisting of a sodium salt, a potassium salt, a magnesium salt, a chromium salt and a calcium salt.

8. The method of claim 5, wherein administration of the composition of HMB increases muscle mass.

9. A method of promoting the export of glycerol from adipocytes by increasing intracellular lipolysis in an animal in need thereof comprising administering to the animal a composition of from about 0.5 g to about 30 g of β-hydroxy-β-methylbutyric acid (HMB) thereby promoting the export of glycerol from adipocytes by increasing intracellular lipolysis.

10. The method of claim 9, wherein said HMB is selected from the group consisting of its free acid form, its salt, its ester, and its lactone.

11. The method of claim 9, wherein said salt is selected from the group consisting of a sodium salt, a potassium salt, a magnesium salt, a chromium salt and a calcium salt.

12. A method of treating at least one of the comorbidities associated with obesity in an animal in need thereof by increasing intracellular lipolysis comprising administering to the animal a composition of from about 0.5 g to about 30 g of β-hydroxy-β-methylbutyric acid (HMB) thereby treating or preventing at least one of the comorbidities associated with obesity by increasing intracellular lipolysis.

13. The method of claim 12, wherein the comorbidities are selected from the group consisting of Type 2 diabetes, cardiovascular disease, chronic inflammation, and cancer.

14. The method of claim 1, wherein the composition is administered to an obese or overweight animal.

15. The method of claim 1, wherein the composition is administered with a hypocaloric diet.

16. The method of claim 1, wherein the composition is administered without caloric restriction.

* * * * *